(12) United States Patent
Rhoda et al.

(10) Patent No.: US 8,668,740 B2
(45) Date of Patent: Mar. 11, 2014

(54) EXPANDABLE VERTEBRAL PROSTHESIS

(71) Applicants: William Rhoda, Media, PA (US); Noah Hansell, King of Prussia, PA (US); Andrew Lee, Santa Rosa, CA (US)

(72) Inventors: William Rhoda, Media, PA (US); Noah Hansell, King of Prussia, PA (US); Andrew Lee, Santa Rosa, CA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 13/648,078

(22) Filed: Oct. 9, 2012

(65) Prior Publication Data

US 2013/0030536 A1 Jan. 31, 2013

Related U.S. Application Data

(63) Continuation of application No. 12/691,350, filed on Jan. 21, 2010, now Pat. No. 8,308,802.

(51) Int. Cl.
*A61F 2/44* (2006.01)

(52) U.S. Cl.
USPC ............... 623/17.15; 623/17.16; 606/105

(58) Field of Classification Search
USPC ........................................ 623/17.11–17.16
See application file for complete search history.

(56) References Cited

U.S. PATENT DOCUMENTS

| 4,932,975 A * | 6/1990 | Main et al. ............. 623/17.12 |
| 6,752,832 B2 * | 6/2004 | Neumann ............... 623/17.15 |

FOREIGN PATENT DOCUMENTS

CA       2524066 A1 * 11/2004

\* cited by examiner

*Primary Examiner* — Andrew Yang

(57) ABSTRACT

The present invention relates to an expandable prosthetic implant device for engagement between vertebrae generally comprising an inner member, outer member, and gear member positioned coaxial with respect to each other such that the inner and outer members are moveable relative to each other along an axis. The gear member is axially fixed to the outer member and freely rotatable with respect to the outer member and the gear member threadedly engages a threaded portion of the inner member to translate inner member along the axis. The implant is configured to engage the vertebrae in a predetermined alignment and the gear member includes gear teeth exposed to the exterior and configured to be accessible by a tool member at a plurality of angular positions around the perimeter of the implant device.

20 Claims, 10 Drawing Sheets

EXPANDABLE VERTEBRAL PROSTHESIS

CROSS-REFERENCE TO RELATED APPLICATIONS

This application is a continuation of U.S. patent application Ser. No. 12/691,350 filed on Jan. 21, 2010, which is a continuation application which claims priority to U.S. application Ser. No. 11/110,844 filed on Apr. 10, 2005 which is incorporated herein in its entirety by reference.

FIELD OF THE INVENTION

The present invention relates to a device to support the spine after removal of at least a part of a vertebra.

BACKGROUND OF THE INVENTION

When a vertebra is damaged or diseased, surgery may be used to replace the vertebra or a portion thereof with a prosthetic device to restore spinal column support. For example, vertebral body replacement is commonly required in the treatment of vertebral fracture, tumor, or infection.

In recent years, several artificial materials and implants have been developed to replace the vertebral body, such as, for example, titanium cages, ceramic, ceramic/glass, plastic or PEEK, and carbon fiber spacers. Recently, various expandable prosthetics or expandable cages have been developed and used for vertebral body replacement. The expandable prosthetic devices are generally adjustable to the size of the cavity created by a corpectomy procedure and typically are at least partially hollow to accommodate bone cement or bone fragments to facilitate fusion in vivo. Some expandable prosthesis may be adjusted prior to insertion into the cavity, while others may be adjusted in situ. One advantage of the vertebral body replacement using an expandable prosthetic device that is adjustable in situ is that it is easy to place or insert because it permits an optimal, tight fit and correction of the deformity by in vivo expansion of the device. Some other advantages offered by an expandable prosthetic device are that they can facilitate distraction across the resected vertebral defect for correction of the deformity, and allow immediate load bearing after corpectomy.

Instrumentation and specialized tools for insertion of a vertebral implant is one important design parameter to consider when designing a vertebral prosthesis. Spinal surgery procedures can present several challenges because of the small clearances around the prosthetic when it is being inserted into position. Another important design consideration includes the ability of the device to accommodate various surgical approaches for insertion of the vertebral implant.

SUMMARY OF THE INVENTION

The present invention relates to an expandable prosthetic implant device for engagement between vertebrae generally comprising an inner member, outer member, and gear member positioned coaxial with respect to each other such that the inner and outer members are moveable relative to each other along an axis. The inner member has a hollow interior portion and a threaded external portion and includes a first end portion configured to engage a first vertebral body. The outer member has a hollow interior portion configured to receive the inner member and includes a second end portion configured to engage a second vertebral body. The gear member is axially fixed to the outer member and freely rotatable with respect to the outer member and the gear member threadedly engages the threaded portion of the inner member.

The implant is configured to engage the vertebrae such that first and second end portions are oriented in a predetermined alignment with respect to the first and second vertebral bodies. The gear member includes gear teeth extending around the perimeter of the gear member and the gear teeth are exposed to the exterior and configured to be accessible by a tool member at a plurality of angular positions around the perimeter.

In one embodiment, the outer member includes a plurality of tool location holes for receiving a portion of a tool member therein to facilitate insertion, alignment and engagement of the tool member with the gear teeth. In another variation, the outer member includes a resiliently deformable portion for receiving the gear member thereon. In yet another embodiment, the inner member, outer member, and gear member may be made of a PEEK plastic material. In another embodiment, the device also includes a locking member for fixing the inner member with respect to the outer member.

In one embodiment, the inner member is rotationally fixed with respect to the outer member. In one variation, the inner member includes a slot and a pin extends radially inward from the outer member to engage the slot to prevent rotational movement of the inner member with respect to the outer member.

In another embodiment, the first end portion may comprise a first plate having a generally oblong shape when viewed perpendicular to the longitudinal axis, the first plate extending a width distance along a long axis and a depth distance along a short axis, wherein the width distance is larger than the depth distance. Similarly, in another embodiment, the second end portion may comprise a second plate having a generally oblong shape when viewed perpendicular to the longitudinal axis, the second plate extending a width distance along a long axis and a depth distance along a short axis, wherein the width distance is larger than the depth distance. In one variation, the first and second end plates include at least one bone engaging member extending longitudinally from the end plates. The bone engaging members may comprise metal spikes.

In another variation, end portions have a thickness in the longitudinal direction and the thickness is variable in the anterior-posterior direction along the short axis. In one embodiment, the thickness varies gradually in the anterior-posterior direction such that the end portion defines a general wedge-shaped profile. In another embodiment, the end portion extends in the anterior-posterior direction from an anterior side to a posterior side and the first end portion has a first thickness at an anterior side and a second thickness at a posterior side, wherein the first thickness is greater than the second thickness. In yet another embodiment, the end portion includes a bone engaging surface and a plane tangent to the bone engaging surface intersects a plane normal to the longitudinal axis at a first angle. In one variation, the angle is between about −16 degrees and about 16 degrees.

BRIEF DESCRIPTION OF THE DRAWINGS

The invention will be more readily understood with reference to the embodiments thereof illustrated in the attached drawing figures, in which.

Throughout the drawing figures, it should be understood that like numerals refer to like features and structures.

DETAILED DESCRIPTION OF THE PREFERRED EMBODIMENTS

Figure 1:
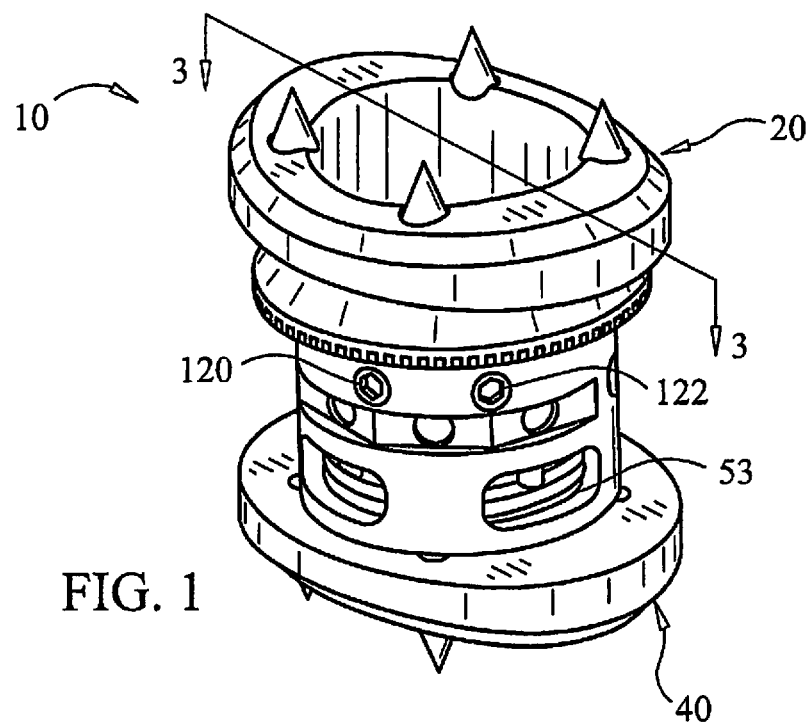
FIG. 1 is a perspective view of a prosthetic device in accordance with an embodiment of the invention.

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Referring to FIGS. 1-9, one embodiment of an expandable vertebral prosthetic device 10 is shown. Prosthesis 10 generally comprises an inner member 12 which may be telescopingly received within an outer member 14. The prosthesis 10 further comprises a gear member 16 generally configured to effect translation of inner member 12 with respect to outer member 14 and cause expansion of prosthesis 10. Inner member 12, outer member 14, and gear member 16 are centered along a longitudinal axis 18 and define a hollow interior portion which may be filled with bone material, bone growth factors, bone morphogenic proteins, or other materials for encouraging bone growth, blood vessel growth or growth of other tissue through the many apertures in the device. In one embodiment, members 12, 14, and 16 are made of a polyether ether ketone (PEEK) plastic material. Several known advantages of PEEK plastic material include that it is radiolucent and may be more easily sterilized than other plastics. In alternate embodiments, members 12, 14, and 16 may be made of a biologically inert metal alloy or other suitable materials.

Referring to FIGS. 1-4, inner member 12 has an endplate 20 at a distal end 22 connected to a generally cylindrical body 24 at a proximal end 26 and generally defines a hollow interior portion extending axially therethrough. Body 24 of inner member 12 generally comprises a wall 27 with an inner surface 28 and an outer surface 30 and at least part of outer surface 30 includes external threads 32. Outer diameter 34 of body 24 is dimensioned to be cooperatively received within outer member 14.

Outer member 14 has an endplate 40 at a proximal end 42 connected to a generally cylindrical body 44 at a distal end 46 and generally defines a hollow interior portion extending axially therethrough. Body 44 of outer member 14 generally comprises a wall 47 with an inner surface 48 and an outer surface 50. Inner diameter 52 of body 44 is dimensioned to cooperatively receive body 24 of inner member 12 within outer member 14. In this regard, inner diameter 52 of body 44 is greater than outer diameter 34 of body 24 of inner member 12. As shown in FIG. 1, outer member 14 may include one or more openings 53 to permit bone ingrowth. According to one embodiment, a lip 54 is formed around the exterior of the distal end 46 of body 44 and is configured to cooperatively fit with a portion of gear member 16. A plurality of relief spaces or slots 56 extending through wall 47 are angularly spaced around body 44 adjacent distal end 46 to facilitate a snapping engagement of lip 54 with gear member 16. In this regard, slots 56 allow distal end 46 to deform slightly and contract in the radial direction to accommodate gear member 16 to snap on to lip 54.

Figure 3:
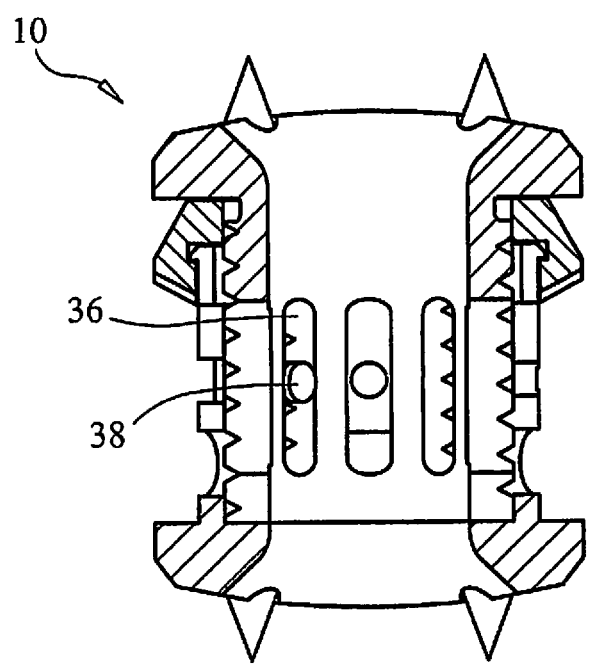
FIG. 3 is a cross-sectional view of the prosthetic device of FIG. 1 taken along line 3-3 of FIG. 1.
Figure 2:
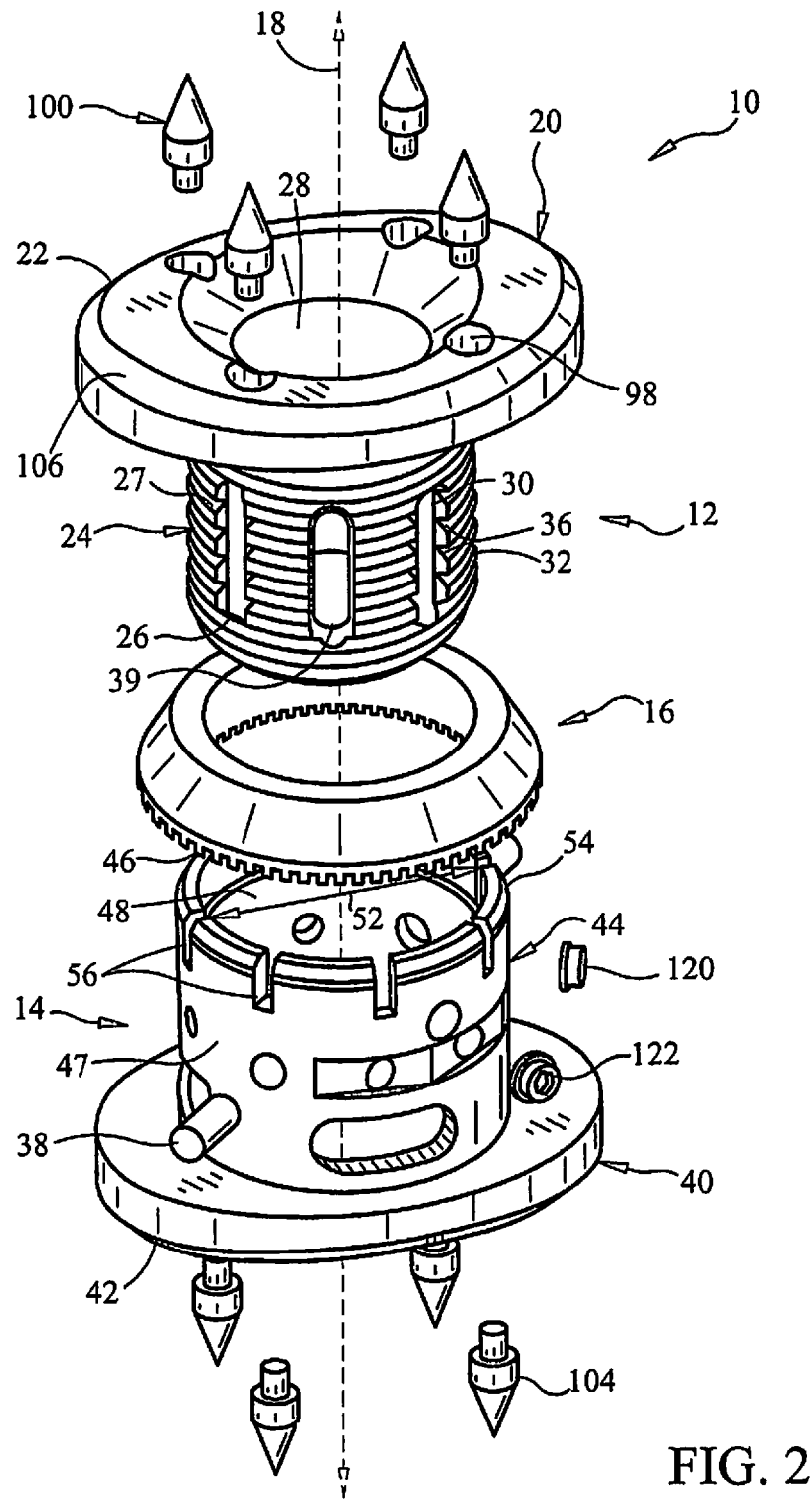
FIG. 2 is an exploded view of the prosthetic device of FIG. 1.
Figure 4:
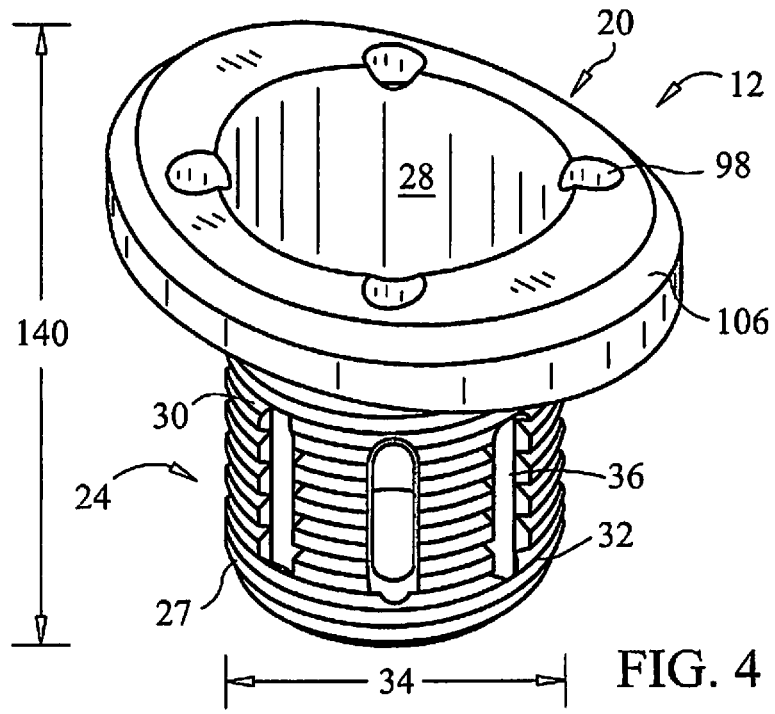
FIG. 4 is perspective view of an embodiment of an inner member of the prosthetic device of FIG. 1.
Figure 5:
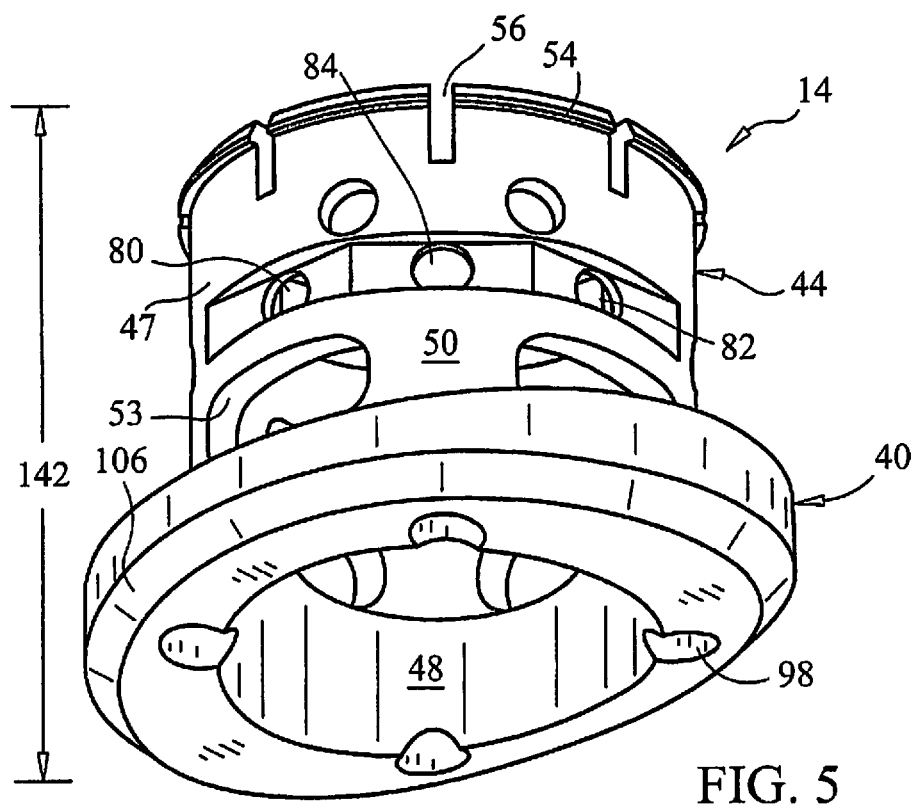
FIG. 5 is perspective view of an embodiment of an outer member of the prosthetic device of FIG. 1.

As best seen in FIGS. 2-4, in one embodiment of a prosthetic device 10, inner member 12 includes a plurality of longitudinal slots 36 extending radially through wall 27. Slots 36 are angularly spaced around body 24 and extend longitudinally along wall 27. When inner member 12 is assembled within outer member 14, slots 36 are configured to engage at least one pin 38 protruding radially inward from the inner surface 48 of outer member 14 to prevent rotational movement of inner member 12 with respect to outer member 14. In this regard, pin 38 may extend into one of slots 36 and may ride within one of the longitudinal slots 36 during expansion of the prosthetic device 10 to prevent rotation of inner member 12 with respect to outer member 14. In addition, pin 38 may prevent inner member 12 from expanding or translating along axis 18 beyond a predetermined distance when pin 38 bottoms out or contacts the proximal end 39 of the slot in which it is engaged.

Figure 7:
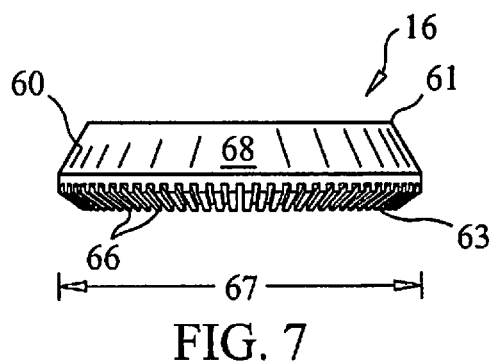
FIG. 7 is an elevated side view of one embodiment of a gear member of the prosthetic device of FIG. 1.
Figure 8:
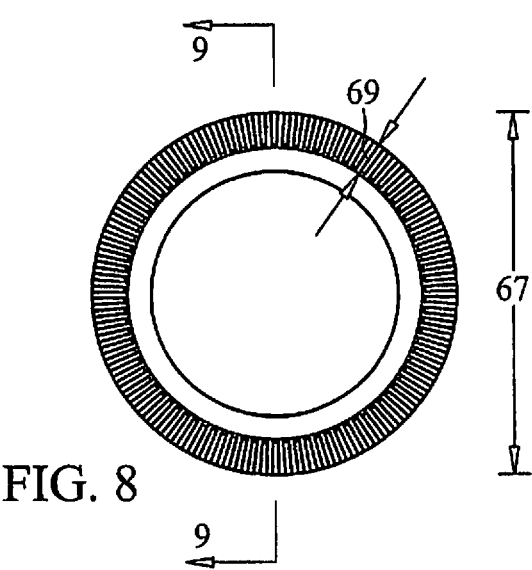
FIG. 8 is an end view of the gear member of FIG. 7.
Figure 9:
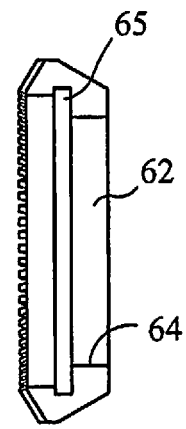
FIG. 9 is a cross-sectional view of the gear member of FIGS. 7 and 8 taken along line 9-9 of FIG. 8.

Referring to FIGS. 7-9, gear member 16 comprises a generally hollow body 60 extending from a distal end 61 to a proximal end 63 with a helical thread 62 along at least part of an inner wall 64 and an array of gear teeth 66 along a portion of the exterior wall 68. Gear member 16 is generally configured to rotatably connect to distal end 46 of outer member 14 and internal helical thread 62 is configured to engage external threads 32 of inner member 12 to cause translation of inner member 12 with respect to outer member 14. In one embodiment, gear member 16 includes a cylindrical cutout feature 65 extending around the inner wall 64 to cooperatively receive lip 54 of outer member 14. In this regard, gear member 16 may rotate freely with respect to outer member 14 while being retained from longitudinal and lateral movement. In this regard, the aforementioned snap-on feature allows for the design and manufacture of a relatively thin walled outer member 14 to facilitate the creation of a larger inner diameter of outer gear member 16 and inner member 12. As a result, more bone growth stimulating material may be packed into the prosthetic device 10. Also, by creating a larger inner diameter of gear member 16 and inner member 12, a larger thread size for external thread 32 and internal thread 62 may be utilized to provide greater mechanical strength.

Figure 6:
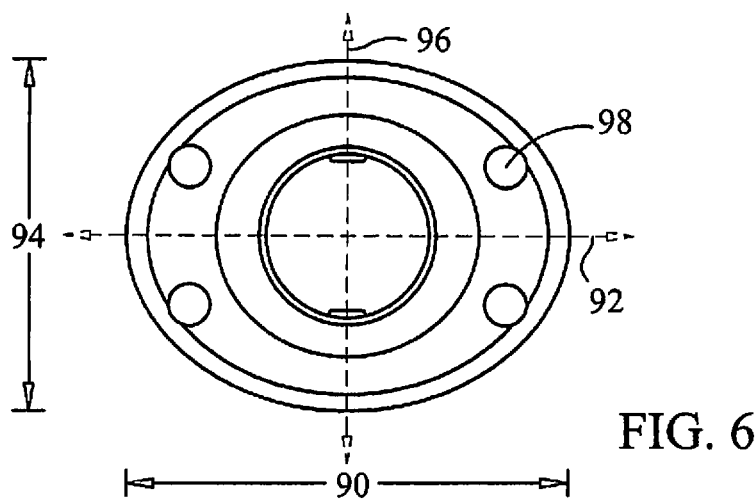
FIG. 6 is an end view of the prosthetic device of FIG. 1.

Referring to FIG. 7, gear teeth 66 are positioned at an angle with respect to the proximal end 63 and extend around the entire periphery of a portion of exterior wall 68 to form a general frusto-conical gear teeth surface adjacent the proximal end 63. The outer-most external diameter 67 of gear member 16 is sized to be the same as or slightly smaller than the smallest outer diameter of endplates 20, 40. In this regard, when prosthetic device 10 is viewed from the end in a plane perpendicular to longitudinal axis 18, as shown in FIG. 6, gear member 16 does not protrude radially outward from beyond the perimeter of endplates 20, 40. In one embodiment, the outer-most diameter of gear member 16 is substantially the same size as the smallest outer diameter of endplates 20, 40. As shown in FIG. 7, in one embodiment gear teeth 66 extend a width 69 in a generally radial direction and generally extend radially outward to the outer diameter of gear member 16. In this regard, teeth 66 may be designed to have a width 69 to accommodate the expected gear forces given the particular bevel gear ratio, types of material used, and desired overall inner diameter of prosthetic device 10. One skilled in the art will appreciate that the larger the outer diameter to which teeth 66 radially extend, the larger that teeth 66 may be designed while still maintaining the same gear ratio. In this regard, when teeth 66 are made larger, they generally have a better mechanical strength. Also, the ability to design larger, wider, and stronger teeth 66 is advantageous for embodiments wherein prosthesis 10 is made of PEEK, other plastic, or other non-metallic materials that may have less mechanical strength than, for instance, titanium. Furthermore, as described in one embodiment, because the outer-most diameter of gear member 16 may be as large as the smallest outer diameter of endplates 20, 40, and teeth 66 extend radially to the outer-most diameter of gear member 16, a larger inner diameter of gear member 16 may be manufactured without compromising mechanical gear strength. As a result, a larger overall inner diameter of prosthetic device 10 may be accommodated which allows the packing of more bone material therein and facilitates bone fusion once prosthetic 10 is implanted.

As seen in FIGS. 1 and 2, in one embodiment teeth 66 are substantially exposed to the exterior of prosthetic device 10. Because teeth 66 are exposed around the periphery, less material is needed to cover up the exposed teeth, which generally makes the prosthetic 10 lighter and easier to manufacture than prior art devices that require covering the gear teeth. In addition, the gear member 16 is more easily visible by a surgeon and more readily accessible by a rotation tool than devices that hide or cover gear teeth. As discussed in more detail below, such a feature allows, inter alia, a tool to engage teeth 66 at a multitude of angular positions around the periphery of outer member 14 to provide a surgeon with various surgical options for insertion of prosthetic device 10. Furthermore, the snap-on assembly feature of gear member 16 allows for the manufacture of thinner walled parts without sacrificing mechanical strength. As a result, prosthesis 10 is able to have a larger internal diameter which allows more space for bone-packing material.

Figure 10:
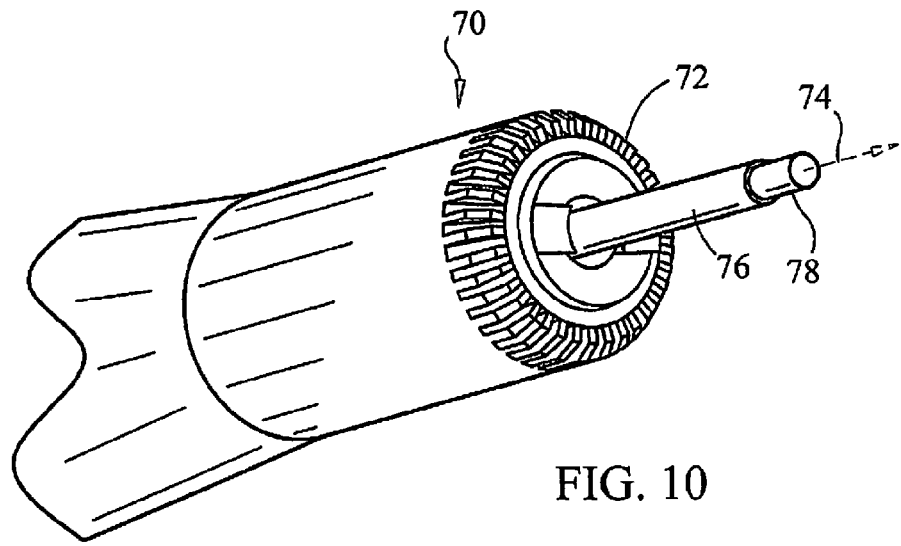
FIG. 10 is a perspective of one embodiment of a tool according to the present invention.
Figure 11:
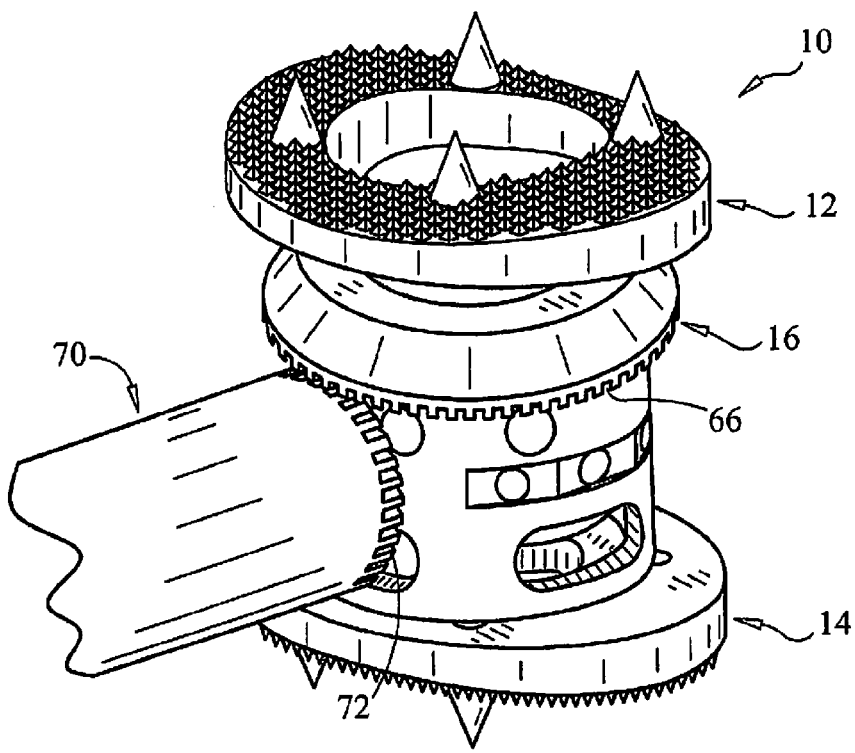
FIG. 11 is a perspective view of the tool of FIG. 10 shown engaging an embodiment of an expandable prosthetic device according to the invention.
Figure 12:
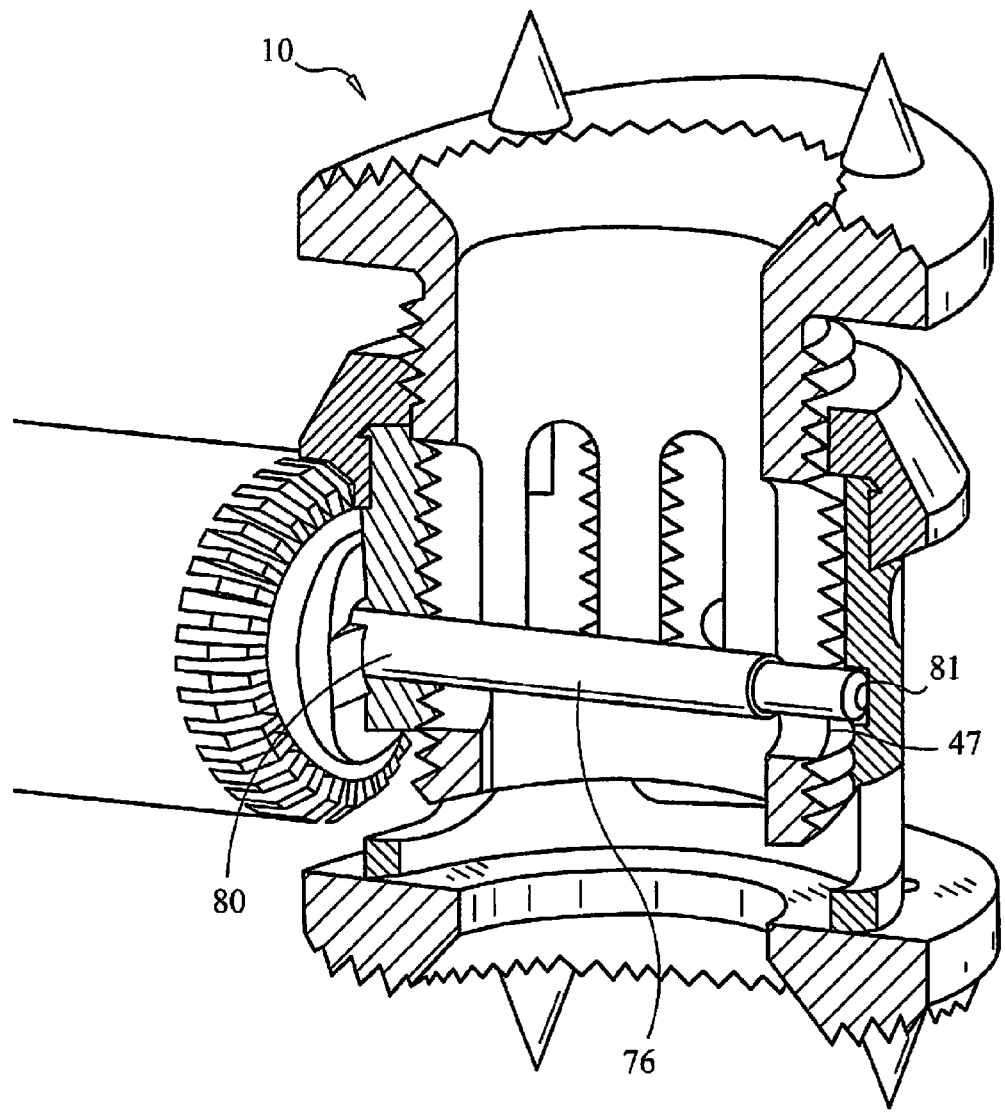
FIG. 12 is a partial cross-sectional view of the combination of FIG. 11.

As shown in FIGS. 10-12, prosthesis 10 may be expanded by a tool 70 that includes a bevel gear 72 at its distal end. Tool 70 extends along a tool axis 74 and in operation tool 70 is configured to engage prosthetic device 10 such that tool axis 74 is generally perpendicular to longitudinal axis 18. Bevel gear 72 is configured to engage teeth 66 of gear member 16 such that when bevel gear 72 is rotated about the axis of the tool, gear member 16 of prosthetic 10 is rotated about longitudinal axis 18 and inner member 12 translates along longitudinal axis 18 to expand prosthesis 10. In one embodiment, tool 70 may include a central shaft 76 having a threaded distal tip portion 78 that extends distally beyond bevel gear 72 to facilitate location and mounting of tool 70 with prosthetic 10. Threaded distal tip portion 78 may be configured to extend radially through a tool location hole 80 in outer member 14 and threadedly engage a threaded hole 81 located on the inner surface 48 of wall 47 positioned diametrically opposite hole 80 to fix the central shaft 76 of tool 70 to outer member 14. Once central shaft 76 is fixed to outer member 14, bevel gear 72 may rotate with respect to central shaft 76 to effect rotation of gear member 16 and translation of inner member 12.

Referring again to FIGS. 2 and 4, in one embodiment of prosthetic device 10 a plurality of mounting features or tool location holes 80, 82, 84 are provided along the outer surface 50 of outer member 14. Tool location holes 80, 82, 84 may be spaced around outer surface 50 in a predetermined arrangement to allow insertion of prosthetic device 10 utilizing different surgical approaches. For example, one skilled in the art will appreciate that holes 80, 82, 84 may be arranged to permit insertion through a lateral approach, anterolateral approach, or an anterior approach. As shown in FIG. 4, tool location hole 80 is angularly located or positioned on wall 47 toward the front of prosthetic 10 or toward the short end of end plates 20, 40 to facilitate insertion of prosthetic device 10 into a patient via an anterior approach. Tool location hole 82 may be angularly located or positioned on wall 47 to be toward the side of prosthetic 10 or toward the long end of end plates 20, 40 to facilitate insertion of prosthetic device 10 into a patient via a lateral approach. In addition, a third tool location hole 84 may be angularly located or positioned to be between location holes 80 and 82 to facilitate insertion of prosthetic device 10 through an anterolateral approach. As described previously, for each location hole 80, 82, 84, a corresponding threaded hole 81, 83, 85 may be formed on the inner surface 48 of wall 47 and positioned diametrically opposite the corresponding tool location hole to permit the threaded engagement of distal tip portion 78 of tool 70.

As best seen in FIGS. 1, 2 and 4, a locking member 120 may be provided to substantially restrict all relative movement between inner member 12 and outer member 14, when, for example, the desired expansion of the prosthetic device 10 has been obtained. In one embodiment of the locking member 120 according to the invention, a portion of locking member 120 may protrude radially inward from the outer member 14 to engage the external surface 30 or thread 32 of inner member 12 and lock or fix inner member 12 to outer member 14 by friction and/or deformation of external threads 32. An internal locking screw 121 may be provided internal to locking member 120 to translate the locking member radially inward when the screw 121 is rotated. Screw 121 may be provided with a hexagonal head at its externally exposed end to facilitate engagement with an allen wrench or other tool to rotate screw 121 and drive locking member 120 radially inward to lock inner member 12 in place. In one embodiment, a plurality of locking members 120, 122, 124 may be provided spaced around the periphery of outer member 14 such that a surgeon can easily extend the locking member when utilizing any one of the aforementioned tool location holes 80, 82, 84.

Referring to FIGS. 1-9, one embodiment of end plates 20, 40 is shown wherein each end plate has a generally oblong or elliptical shape when viewed from the end or perpendicular to the longitudinal axis 18. As shown in FIG. 6, each end plate 20, 40 generally extends a width distance 90 (large outer diameter) along a long axis 92 in a medial-lateral direction and a length distance 94 (small outer diameter) along a short axis 96 in the anterior posterior direction, wherein width 90 is larger than the length 94. The oblong or elliptical shape of end plates 20, 40 is designed to resemble or mimic the footprint of the vertebral body to which the end plates will engage. In this regard, end plates 20, 40 are configured to engage portions of the vertebrae in a predetermined orientation, namely with long axis 92 extending in a medial-lateral direction, to maximize contact of the superior surface of the end plates 20, 40 with bone.

Figure 13:
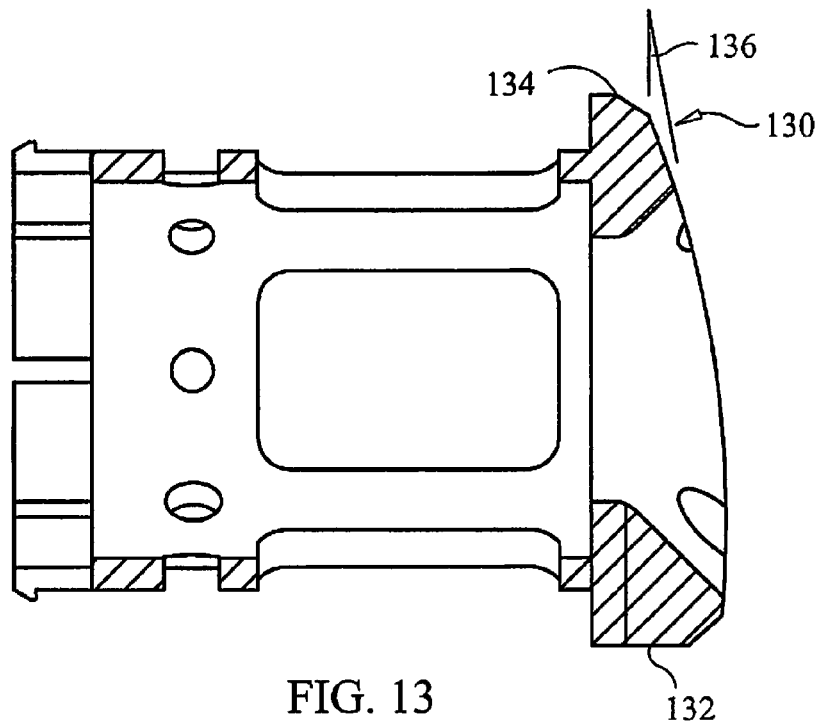
FIG. 13 is a cross-sectional view of another embodiment of an outer member according to the invention.

The dimensions of end plates 20, 40 can be varied to accommodate a patients anatomy. Typically, end plates 20, 40 may have a width between about 14-32 mm (in the medial-lateral direction) and a length between about 12-25 mm (in the anterior-posterior direction). In some embodiments, implants 20, 40 have a wedge-shaped profile to accommodate the natural curvature of the spine. For example, as shown in FIG. 13, one embodiment of a wedge shape is shown wherein the end plate 130 has a gradual decrease in height from an anterior side 132 to a posterior side 134. In anatomical terms, the natural curvature of the lumbar spine is referred to as lordosis. When prosthetic device 10 is to be used in the lumbar region, the angle 136 formed by the wedge should be approximately between 4 degrees and 16 degrees so that the wedge shape is a lordotic shape which mimics the anatomy of the lumbar spine. In alternate embodiments, the wedge shape profile may result from a gradual increase in height from anterior side 132 to posterior side 134 to mimic the natural curvature in other regions of the spine. Thus, in other embodiments, angle 136 may be between about −4 degrees and −16 degrees.

As shown in FIGS. 1 and 2, a plurality of mounting holes 98 are spaced around the perimeter of each end plate 20, 40 for receiving insertable bone engaging members 100. In one embodiment, bone engaging members 100, comprise conical spikes 102 each having a cylindrical base portion 104 configured to fit within holes 98, for instance by press-fit. In alternate embodiments, differently shaped bone engaging members 100 may be used, or in other embodiments no bone engaging members may be used. Referring again to FIG. 2, according to one embodiment, end plates 20, 40 have chamfered edges 106 around the perimeter to facilitate insertion and/or accommodate the shape of the vertebral bodies which they engage. The superior or bone engaging surface 108 of endplates 20, 40 may also include numerous types of texturing to provide better initial stability and/or grasping contact between the end plate and the respective vertebrae.

The dimensions of prosthetic device 10 in accordance with the invention may be as follows, although the dimensions of the embodiments shown in the figures are not critical to the invention. In one embodiment, inner member 12 may have a total height 140 of between about 13-68 mm, outer member may have a total height 142 of between about 11-64 mm, and prosthetic device 10 may be extended to a total prosthetic height of between about 15-130 mm, depending on the configuration and desired application.

In alternate embodiments, the length, diameter, and shape of prosthetic device 10 may vary to accommodate different applications, different procedures, implantation into different regions of the spine, or size of vertebral body or bodies being replaced or repaired. For example, prosthetic device 10 may be expandable to a longer distance to replace multiple vertebral bodies. Also end plates 20, 40 can be sized and shaped to accommodate different procedures. For example, end plates 20, 40 may be made smaller for smaller statured patients or for smaller regions of the cervical spine. In addition, it is not required that end plates 20, 40 be shaped and sized identically and in alternate embodiments they can be shaped or sized differently than each other and/or include different bone engaging members or texturing.

Figure 14:
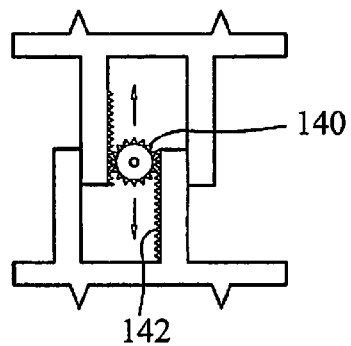
FIGS. 14-25 depict various alternate embodiments of expandable prosthetic devices according to the present invention.
Figure 15:
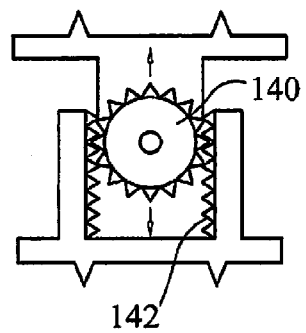
Figure 16:
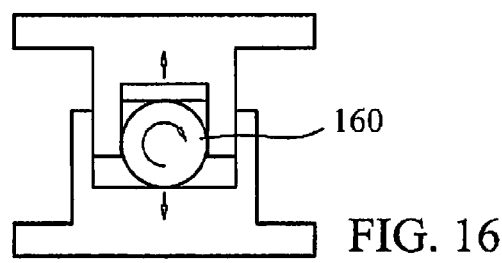
Figure 17:
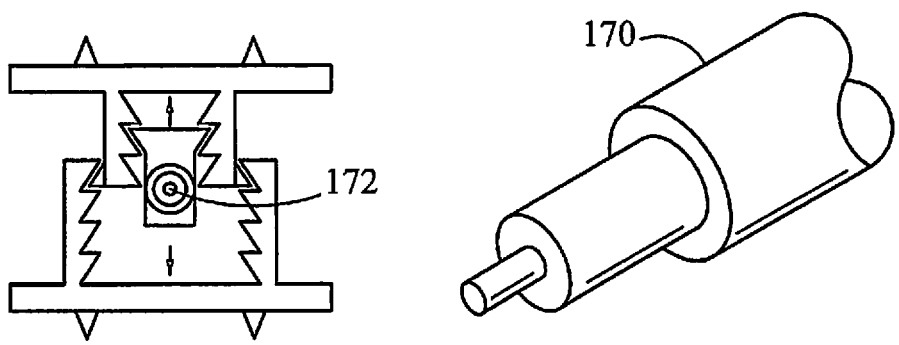
Figure 18:
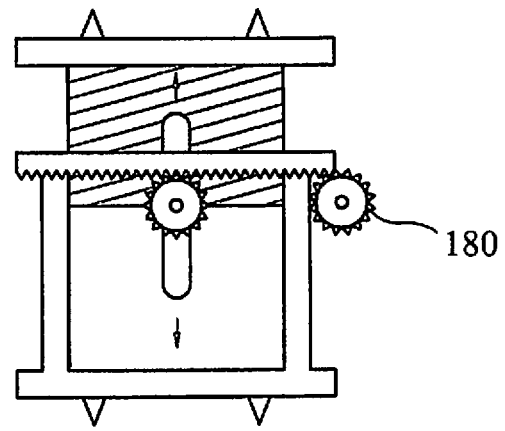
Figure 19:
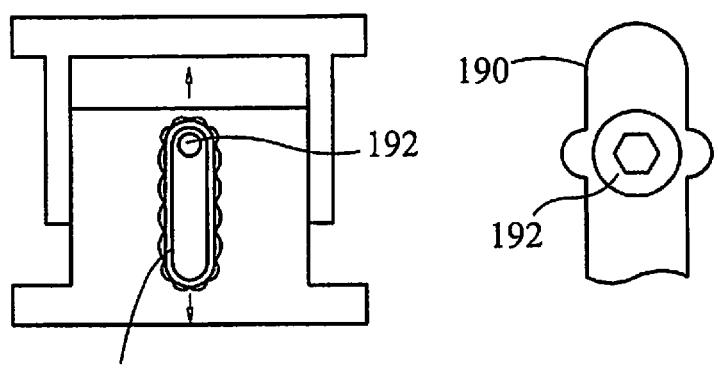
Figure 20:
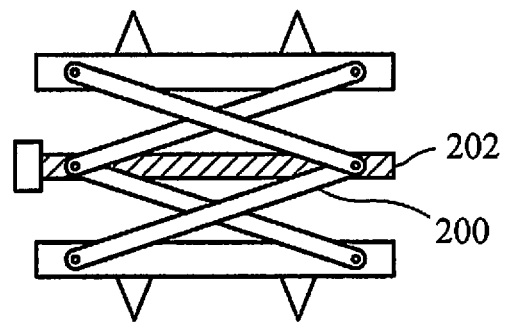
Figure 21:
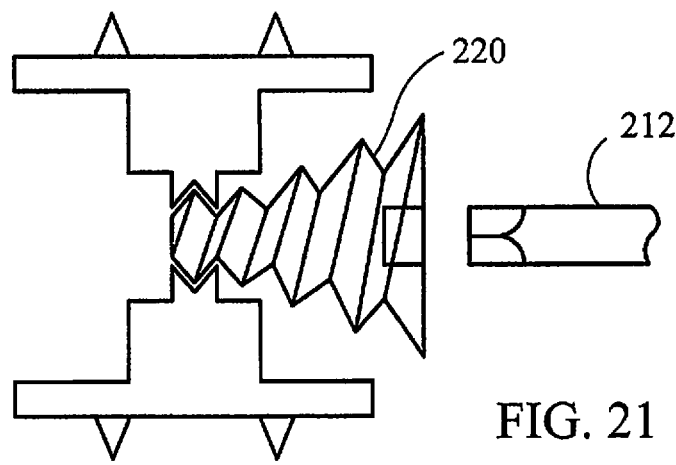
Figure 22:
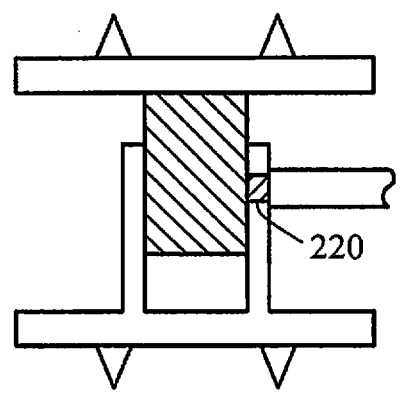
Figure 23:
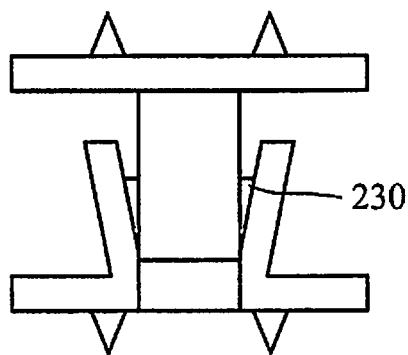
Figure 24:
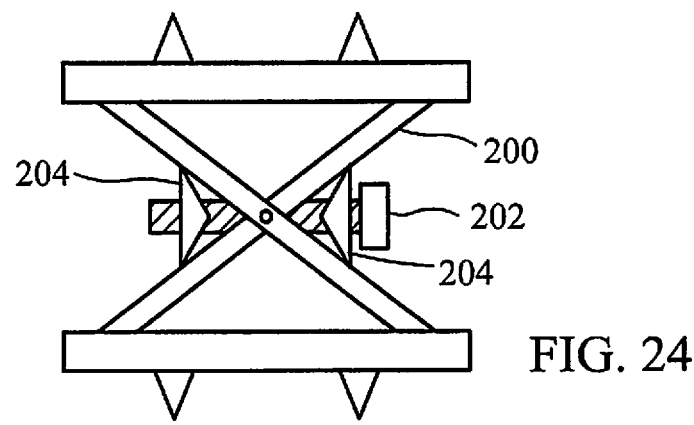
Figure 25:
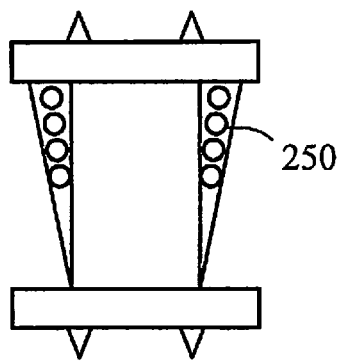

Referring to FIGS. 14-25, various alternate embodiments of expandable prosthetic devices according to the present invention are shown. Referring to FIGS. 14 and 15, in one variation a central gear member 140 may be positioned between the inner and outer members to engage teeth 142 to facilitate expansion. Referring to FIG. 16, in another embodiment an oblong cam 160 may be used to facilitate expansion. As shown in FIG. 17, an eccentric driver 170 may be used to mate with an oblong hole 172 to provide expansion. As shown in FIG. 18, in another embodiment an alternate worm gear 180 can be used. Referring to FIG. 19, a slot 190 with a cam lock 192 may be used to expand and lock the device at a certain expansion distance. Referring to FIGS. 20 and 24, in other embodiments, a scissor jack 200 and threaded screw 202 may be used to facilitate expansion. As shown in FIG. 24, a wedge 204 may be used to engage the scissor jack 200. Referring to FIGS. 21 and 22, alternate threaded devices may be used to expand the prosthetic device. As shown in FIG. 21, a tapered screw 210 may be used that may be driven by a driver 212. Alternatively, as shown in FIG. 22, a simple screw threaded engagement between the inner member and outer member may used. Also a set screw 220 may be used to lock the device at a certain expansion distance. Referring to FIGS. 23 and 25, the inner and outer members may be shaped to ride along an inclined plane or ramp. As shown in FIG. 23, a locking wedge or ring 230 may be provided to lock the device at a certain expansion distance. As shown in FIG. 25, rollers 250 may be provided to facilitate expansion of the device.

FIGS. 26-29 illustrates an self-locking mechanism applied to the expandable prosthesis. As mentioned in the previous drawings, FIG. 26 likewise illustrates a prosthesis having an upper and lower endplates. The upper endplate is attached to an inner member and the lower endplate is attached to the outer member. The inner member is threaded and translatable along the longitudinal axis. A gear member that is provided with internal threads is utilized to translate the inner member along the longitudinal axis.

The self locking mechanism of the present invention is operational by having a lever integrated with the entire assembly in which it is fixed to the base and configured to move radially within a fixed space to engage or disengage with the gear. The lever in its it's neural position is engaged within the notices on the inside of the gear. When the inserter is placed into the implant, the aligning portion of the inserter pushed on the lever causing it to move distally towards the center of the implant such that it is no longer engaged with the notches of the gear and thus allowing the gear to spin. When the inserter is removed, the locking lever returns to the neural position thus locking the gear from turning. The present locking mechanism prevents the entire mechanism from loosening or gaining height situ. More specifically, the present locking mechanisms prevents the gear from turning once the height of the implant is set.

While the invention herein disclosed has been described by means of specific embodiments and applications thereof, numerous modifications and variations can be made thereto by those skilled in the art without departing from the scope of the invention as set forth in the claims.

What is claimed is:

1. An expandable prosthetic implant device for engagement between vertebrae, comprising:
   an inner member having a hollow interior portion and a threaded external portion and including a first end portion configured to engage a first vertebral body;
   an outer member having a hollow interior portion configured to coaxially receive the inner member therein and including a second end portion configured to engage a second vertebral body, wherein the inner and outer members are moveable relative to each other along a longitudinal axis;

a gear member positioned coaxial to the inner member and outer member and axially fixed to the outer member and freely rotatable with respect to the outer member, wherein the gear member threadedly engages the threaded portion of the inner member, wherein the inner member comprises a longitudinal slot extending radially through a wall of the inner member and configured to engage at least one pin protruding radially inward from the outer member, wherein the outer member comprises a plurality of reliefs formed on the exterior of a distal end of the outer member and configured cooperatively fit with a portion of the gear member wherein the longitudinal slot is contained between the upper and lower ends of the inner member.

2. The device of claim 1, wherein a plurality of apertures are configured for receiving a portion of a tool member to facilitate insertion, alignment and engagement of the tool member with the gear member.

3. The device of claim 1, wherein the outer member includes a resiliently deformable portion for receiving the gear member thereon.

4. The device of claim 1, wherein the inner member, outer member, and gear member are made of a PEEK plastic material.

5. The device of claim 1, further comprising a locking member for fixing the inner member with respect to the outer member.

6. The device of claim 1, wherein the inner member is rotationally fixed with respect to the outer member.

7. The device of claim 6, wherein the inner member includes a slot and a pin extends radially inward from the outer member to engage the slot to prevent rotational movement of the inner member with respect to the outer member.

8. The device of claim 1, wherein the first end portion comprises a first plate having a generally oblong shape when viewed along the longitudinal axis, the first plate extending a width distance in a medial-lateral direction along a long axis and a depth distance in a anterior-posterior direction along a short axis, wherein the width distance is larger than the depth distance.

9. The device of claim 1, wherein the second end portion comprises a second plate having a generally oblong shape when along the longitudinal axis, the second plate extending a width distance in a medial-lateral direction along a long axis and a depth distance in a anterior-posterior direction along a short axis, wherein the width distance is larger than the depth distance.

10. The device of claim 1, wherein the first and second end plates include at least one bone engaging member extending longitudinally from the end plates.

11. The device of claim 10, wherein the bone engaging members comprise metal spikes.

12. The device of claim 8, wherein the first end portion has a thickness in the longitudinal direction and the thickness is variable in the anterior-posterior direction along the short axis.

13. The device of claim 2, wherein the thickness varies gradually in the anterior-posterior direction such that the first end portion defines a general wedge-shaped profile.

14. The device of claim 2, wherein the first end portion extends in the anterior-posterior direction from an anterior side to a posterior side and the first end portion has a first thickness at an anterior side and a second thickness at a posterior side, wherein the first thickness is greater than the second thickness.

15. The device of claim 4, wherein the first end portion includes a bone engaging surface and a plane tangent to the bone engaging surface intersects a plane normal to the longitudinal axis at a first angle.

16. The device of claim 5, wherein the first angle is between about −16 degrees and about 16 degrees.

17. The device of claim 9, wherein the second end portion has a thickness in the longitudinal direction and the thickness is variable in the anterior-posterior direction along the short axis.

18. The device of claim 7, wherein the thickness varies gradually in the anterior-posterior direction such that the second end portion defines a general wedge-shaped profile.

19. An expandable prosthetic implant device for engagement between vertebrae, comprising:

an inner member having a hollow interior portion and a threaded external portion and including a first end portion configured to engage a first vertebral body;

an outer member having a hollow interior portion configured to coaxially receive the inner member therein and including a second end portion configured to engage a second vertebral body, wherein the inner and outer members are moveable relative to each other along a longitudinal axis;

a gear member positioned coaxial to the inner member and outer member and axially fixed to the outer member and freely rotatable with respect to the outer member, wherein the gear member threadedly engages the threaded portion of the inner member, wherein the inner member comprises a longitudinal slot extending radially through a wall of the inner member and configured to engage at least one pin protruding radially inward from the outer member wherein the longitudinal slot extends between the upper and lower ends of the inner member and contained between the upper and lower ends of the inner member, wherein the outer member comprises a plurality of reliefs formed on the exterior of a distal end of the outer member and configured cooperatively fit with a portion of the gear member.

20. An expandable prosthetic implant device for engagement between vertebrae, comprising:

an inner member having a hollow interior portion and a threaded external portion and including a first end portion configured to engage a first vertebral body;

an outer member having a hollow interior portion configured to coaxially receive the inner member therein and including a second end portion configured to engage a second vertebral body, wherein the inner and outer members are moveable relative to each other along a longitudinal axis;

a gear member positioned coaxial to the inner member and outer member and axially fixed to the outer member and freely rotatable with respect to the outer member, wherein the gear member threadedly engages the threaded portion of the inner member, wherein the implant is configured to engage the vertebrae such that first and second end portions are oriented in a predetermined alignment with respect to the first and second vertebral bodies, wherein the inner member comprises a longitudinal slot extending radially through a wall of the inner member and configured to engage at least one pin protruding radially inward from the outer member, wherein the pin prevents the inner member from expanding or translating along an axis beyond a predetermined distance when the pin contacts a proximal end of the slot wherein the longitudinal slot is contained between the upper and lower ends of the inner member, wherein the outer member comprises a plurality of reliefs formed on the exterior of a distal end of the outer member and configured cooperatively fit with a portion of the gear member.

\* \* \* \* \*